United States Patent [19]
Oikawa et al.

[11] Patent Number: 5,449,728
[45] Date of Patent: Sep. 12, 1995

[54] OPTICALLY ACTIVE ACETYLENE POLYMER, MEMBRANE THEREOF AND OPTICAL RESOLUTION METHOD USING THE SAME

[75] Inventors: Eizo Oikawa; Toshiki Aoki, both of Niigata; Kenichi Shinohara, Kanagawa; Masayuki Kokai, Niigata, all of Japan

[73] Assignee: Daicel Chemical Industries, Ltd., Osaka, Japan

[21] Appl. No.: 211,104

[22] PCT Filed: Sep. 9, 1993

[86] PCT No.: PCT/JP93/01284

§ 371 Date: Mar. 15, 1994

§ 102(e) Date: Mar. 15, 1994

[30] Foreign Application Priority Data

Aug. 31, 1993 [JP] Japan .................. 5-215606

[51] Int. Cl.$^6$ .................. C07F 7/08; C07F 30/08
[52] U.S. Cl. .................. 526/279; 556/489; 562/401; 562/402
[58] Field of Search .................. 526/279; 562/401, 402; 556/489

[56] References Cited

U.S. PATENT DOCUMENTS

| | | | |
|---|---|---|---|
| 3,223,686 | 12/1965 | Natta et al. | 556/489 |
| 4,778,868 | 10/1988 | Higashimura et al. | 526/279 |
| 4,800,162 | 1/1989 | Matson | 435/280 |
| 4,814,475 | 3/1989 | Funahashi et al. | 556/489 |
| 4,837,386 | 6/1989 | Pushpinder | 526/279 |
| 4,902,763 | 2/1990 | Savoca et al. | 526/279 |

FOREIGN PATENT DOCUMENTS

| | | | |
|---|---|---|---|
| 225503 | 6/1987 | European Pat. Off. | 562/401 |
| 62-180701 | 8/1987 | Japan . | |
| 63-238133 | 10/1988 | Japan | 526/279 |
| 63-57083 | 11/1988 | Japan . | |

OTHER PUBLICATIONS

The Guide To Drug Manufacturing, Japan, pp. 97 and 98 (1985).
Kikan Kagaku Sosetsu, (Quarterly Survey of Chemistry), No. 6, 4–5 (1989).
Biotechnology of Amino Acid Production, vol. 24, pp. 269 to 279, Kodansha Ltd., and Elsevier Science Pub. (1986).

*Primary Examiner*—Veronica P. Hoke
*Attorney, Agent, or Firm*—Flynn, Thiel, Boutell & Tanis

[57] ABSTRACT

An optically active acetylene polymer which is obtained by polymerizing an optically active form of 1-[dimethyl(10-pinanyl)silyl]-1-propyne which is represented by the following formula (I) and has a weight-average molecular weight of from 10,000 to 1,000,000, a membrane comprising this optically active acetylene polymer as the main component and a method for optically resolving a mixture of optical isomers by using this membrane:

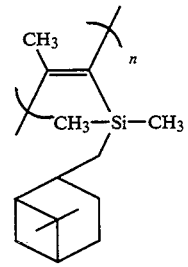

(I)

5 Claims, 1 Drawing Sheet

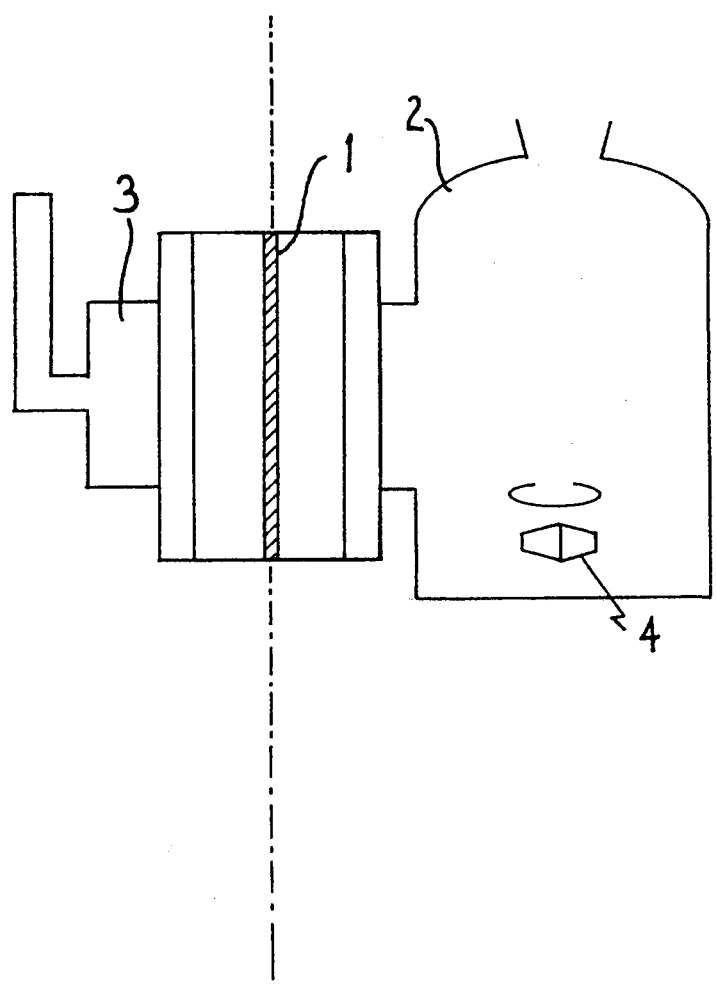

OPTICALLY ACTIVE ACETYLENE POLYMER, MEMBRANE THEREOF AND OPTICAL RESOLUTION METHOD USING THE SAME (FIELD OF THE INVENTION)

This invention relates to a novel optically active acetylene polymer, a membrane thereof and an optical resolution method using the same.

(DESCRIPTION OF THE PRIOR ART)

Many of organic compounds have an asymmetric center. Such an organic compound has optical isomers arising from the asymmetric center. Among optical isomers, optical antipodes (enantiomers) scarcely differ from each other in physical properties including boiling point and solubility. However, it is frequently observed that these antipodes largely differ from each other in physiological activities. It is therefore highly useful in the fields of, for example, drugs, agricultural chemicals and foods to obtain one of the optical isomers (D- or L-form).

In the case of glutamic acid, for example, the L(S)-form has a deliciousness but the D(R)-form lacks any deliciousness. In the case of asparthame which is a sweetener, it is said that the S-form exhibits a sweetness while the R-form exhibits a bitterness.

In the case of drugs, as well, it is sometimes observed that the D-form of a compound significantly differs from the L-form of the same compound in drug effect and toxicity. Accordingly, the Ministry of Health and Welfare describes in the Guide to Drug Manufacturing (1985) that "when the compound exists as a racemic modification, it is desirable to examine the absorption, distribution, metabolism and excretion behaviors of each isomer."

To meet these social needs, there have been devised various means for obtaining optically active forms from racemic modifications.

As examples of methods for obtaining an optically active form from a racemic modification, preferential crystallization, diastereomer method, enzymatic method, chromatographic method and membrane separation technique may be cited.

The preferential crystallization is a method which comprises inoculating a supersaturated solution of a racemic modification with desired crystals, allowing the development exclusively of the inoculated crystals and then precipitating them. Although this is an excellent method, only limited results have been brought thereby. This is because when a racemic modification is to be resolved by the preferential crystallization, it is necessary to examine whether the following factors are satisfied or not: (1) the solubility of the racemic modification in a specific solvent is higher than that of both optical isomers; (2) the melting point of the optically active forms is higher than that of the racemic modification; (3) the optically active forms are insoluble in the supersaturated solution of the racemic modification; and (4) the IR spectra of the racemic modification agree with those of the optically active forms [see Hiroshi Yamanaka and Yasuhisa Tashiro, Kikan Kagaku Sosetsu (Quarterly Survey of Chemistry), No. 6, pages 4–5 (1989)]. Further, it is an important technical problem in the preferential crystallization to timely effect the solid/liquid separation and to shorten the filtration time. Under these circumstances, it may be said that the preferential crystallization is a technique which is applicable exclusively to special crystals, in other words, special compounds.

The diastereomer method is a technique which comprises treating a racemic modification with an optically active acid or base to thereby form optical isomer salts being diastereomeric with each other and separating these optical isomer salts by fractional crystallization by taking advantage of the difference in solubility between these optical isomer salts formed. This method is accompanied by a difficulty in the selection of the resolving agent (the above-mentioned optically active acid or base) capable of easily forming salts or derivatives with the racemic modification. This method also suffers from restrictions such that an optically active form having a high purity can be hardly obtained thereby and that the resolving agent should be used in an equivalent amount to the racemic modification.

In the optical resolution method with the use of an enzyme, the stereospecificity of the enzyme for the substrate is utilized. It is suitable as a method for obtaining an optically active form in a large amount. For example, there has been established a technique for producing a D-amino acid on an industrial scale by the enzymatic method with a combination of a hydantoinase reaction with a chemical decarbamoylation reaction (see S. Takahashi, H. Yamada et al., "Biotechnology of Amino Acid Production", p. 269, Kodansha Ltd., 1986). Further, U.S. Pat. No. 4,800,162 has described a method for obtaining an optically active form by using a capillary-type membrane on which an enzyme has been immobilized. In the case of the enzymatic method, however, it is highly difficult to find out an enzyme fitting for the racemic modification to be optically resolved. Accordingly, this method has a disadvantage that it is applicable only to highly restricted racemic modifications.

The chromatographic method is a method for optically resolving a racemic modification by using a chiral compound as a stationary phase and taking advantage of the interaction of each of the D- and L-forms with the stationary phase (the packing). Thanks to the progress in the high performance liquid chromatography (HPLC) techniques and the development of packings having an excellent capability of optical recognition, there has been enlarged the range of compounds to which the chromatographic method is applicable and the performance of this method has been improved. However, the state of the art is such that it cannot be economically carried out on an industrial scale as yet.

Yamaguchi et al. have examined optical resolution with the use of a separating membrane and disclosed a liquid membrane method with the use of a porous membrane impregnated with a crown compound in Japanese Patent Publication No. 57083/1988 and Japanese Patent Laid-Open No. 180701/1987. However, this optical resolution method of membrane separation has not attained such a level as to be usable as a practical technique so far.

As describes above, each of the above-mentioned optical resolution methods has disadvantages of its own. Therefore it is unavoidable to conclude that any of them is lacking for versatility as a technique for economically obtaining a large amount of an optically active form.

It is the problem to be solved by the present invention to provide a novel optically active polymer which is versatile and has an ability to distinguish optical activity, thus being useful in economically obtaining a large amount of an optically active form, a membrane thereof and an optical resolution method using the same.

DISCLOSURE OF THE INVENTION

In order to solve the above-mentioned problem, the present inventors have conducted intensive studies on an optical resolution method with the use of the membrane separation method. The membrane separation method has been recognized to be of advantage over other methods in energy saving, profitability and operability and thus commonly utilized in the fields of industries and drugs. In the conventional membrane separation method, however, high-molecular weight substances are separated from low-molecular weight ones mainly on the basis of the principle of sieving depending on the size of pores located in the active layer of a membrane. It is therefore impossible to separate substances having the same molecular weight (for example, optical isomers) by the conventional membrane separation method. The present inventors have successfully found out a novel optically active polymer which is usable in the formation of a membrane and has an excellent ability to distinguish optical activity, thus completing the present invention.

Accordingly, the present invention provides an optically active acetylene polymer, which is obtained by polymerizing an optically active form of 1-[dimethyl(10-pinanyl)silyl]-1-propyne and represented by the following formula (I) and has a weight-average molecular weight of from 10,000 to 1,000,000, a membrane comprising this optically active acetylene polymer as the main component and an optical resolution method characterized by optically resolving a mixture of optical isomers by using this membrane.

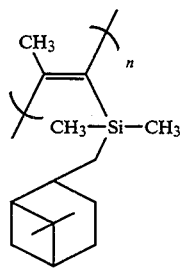

(I)

wherein n represents a number giving a weight-average molecular weight of from 10,000 to 1,000,000.

Now, the present invention will be described in greater detail.

As an example of a method for producing the optically active acetylene polymer of the present invention represented by the formula (I), a method represented by the following reaction scheme may be cited.

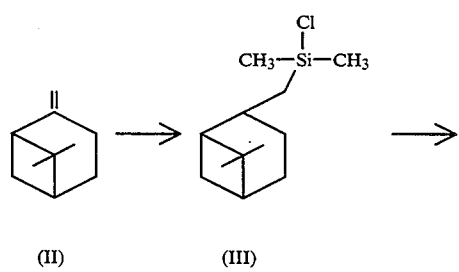

(II)          (III)

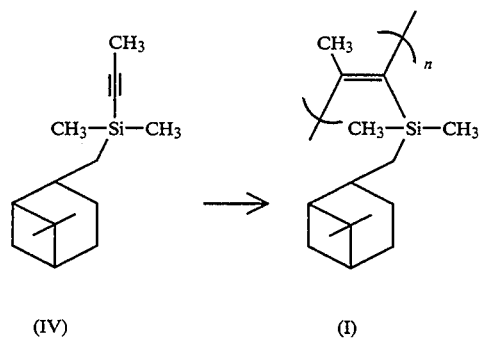

(IV)          (I)

First, an optically active form of β-pinene represented by the formula (II) is reacted with chloromethylsilane in the presence of a catalyst such as $H_2PtCl_6$ to thereby give an optically active form of 10-(chlorodimethylsilyl)pinane represented by the formula (III). Next, this optically active 10-(chlorodimethylsilyl)pinane represented by the formula (III) is reacted with lithiated propyne to thereby give an optically active form of 1-[dimethyl(10-pinanyl)silyl]-1-propyne (hereinafter referred to simply as DPSP) represented by the formula (IV). The DPSP is dissolved in a solvent such as toluene and polymerized in the presence of a catalyst such as tantalum pentachloride at 80° to 100° C. Thus the optically active acetylene polymer represented by the formula (I) [hereinafter referred to simply as poly(DPSP)] is obtained.

From the viewpoints of membrane-forming properties and membrane strength, the weight-average molecular weight of the optically active poly(DPSP) preferably ranges from 10,000 to 1,000,000, still preferably from 50,000 to 800,000. The optically active poly(DPSP) is in the form of a white solid and soluble in organic solvents such as toluene and chloroform. The glass transition point (Tg) of the optically active poly(DPSP) is 148° C. It exists as a glassy polymer at room temperature.

By using the optically active poly(DPSP), a membrane is produced by the solvent casting method. More specifically, the optically active poly(DPSP) is dissolved in a solvent such as toluene to thereby give a solution, which is cast on a sheet, for example, a polytetrafluoroethylene sheet. After evaporating the solvent, the obtained optically active poly(DPSP) membrane is peeled off the sheet and dried.

The optically active poly(DPSP) membrane has an excellent ability to distinguish optical activity and thus can be used in the resolution of various optical isomers. In particular, it can be suitably used in the resolution of optical isomers of, for example, tryptophan, mandelic acid and 2-butanol.

It is conceivable that the optically active poly(DPSP) membrane has asymmetric spaces originating in the pinanyl groups in the gaps between the polymer chains in the membrane. When optical isomers go through these asymmetric spaces, the diffusion rate varies from an enantiomer (optical isomer) to another. That is to say, these spaces seemingly act as a so-called chiral channel. It is conceivable that the selective permeability of an optical isomer in this membrane is thus achieved.

In the present invention, an objective substance can be optically resolved by using an optically active poly(DPSP) membrane in an aqueous solvent system or a methanol solvent system, namely, by using a solution obtained by dissolving the substance in an aqueous solvent system or a methanol solvent system, preferably the latter system.

In the optical resolution with the use of an optically active poly(DPSP) membrane, the selectivity for and permeability to the optical isomers of the membrane can be enhanced by replacing water by methanol to employ as the solvent for dissolving the substance to be optically resolved. The reason therefor is seemingly as follows. The affinity of the polymer of the present invention for methanol is higher than that for water. When methanol is used, therefore, the gaps between the polymer chains in the membrane made from this polymer are widened as compared with a case where water is employed as the solvent. It is conceivable that the gaps between the polymer chains thus widened have a width suitable for the interaction between optical isomer molecules and the polymer.

The optically active acetylene polymer according to the present invention is a material useful in the resolution of optical isomers. A membrane made from this polymer is an excellent optical resolution membrane. It is expected that an optical resolution method using this membrane is highly useful as an industrial means for obtaining an optical isomer. Furthermore, the optical resolution method of the present invention with the use of a methanol solvent system exhibits a high selectivity for and a high permeability to optical isomers.

BRIEF DESCRIPTION OF THE DRAWING

FIG. 1 is a schematic sectional view of a glass permeation cell employed in the optical resolution experiment in the Examples.

In said drawing, 1 stands for a (+)-poly(DPSP) membrane, 2 stands for the feed side of the permeation cell, 8 stands for the permeation side of the cell, and 4 stands for a stirrer.

EXAMPLES

The present invention is further illustrated in greater detail, but no limitation is made into Examples.

Example 1

Preparation of
(+)-poly[1-(dimethyl(10-pinanyl)silyl)-1-propyne)

(1) Preparation of (−)-10-(chlorodimethylsilyl)pinane:

$H_2PtCl_6 \cdot 6H_2O$ (46.5 mg, 89.6 mmol) was dissolved in toluene (24.5 ml) at 80° C. To the solution thus obtained was added chlorodimethylsilane (15.1 g, 160 mmol) at 40° C. Next, (−)-β-pinene (10.9 g, 80.0 mmol) was added thereto at 80° C. and the resulting mixture was stirred for 24 hours. These procedures were all effected in nitrogen gas. The reaction product was purified by distillation at a reduced pressure.

Yield: 89.2%, b.p.: 68° C. (0.30 mmHg).

H-NMR (CDCl$_3$): δ=0.48 [s; 6H, ClSi(CH$_3$)$_2$], 0.92, 1.26 [2s; 6H, gem-(CH$_3$)$_2$], 1.07–2.68 (m; 11H, CH, CH$_2$ pinane skeleton).

(2) Preparation of (−)-1-[dimethyl(10-pinanyl)silyl]-1-propyne [hereinafter referred to simply as (−)-(DPSP)]:

To propyne (4.00 g, 0.10 mol) was slowly added a solution of butyllithium (0.11 mol) in ether (15 ml) at −50° C. The mixture thus obtained was stirred at room temperature for 1 hour and then (−)-10-(chlorodimethylsilyl)pinane (23.1 g, 0.10 mol) was slowly added thereto at 0° C. After putting the obtained mixture in reflux for 24 hours, the reaction mixture was washed with water, dried over anhydrous sodium sulfate and purified by silica gel chromatography (eluent: hexane/chloroform=4/1, v/v).

Yield: 55.9%, Rf=0.73.

$^1$H-NMR (CDCl$_3$): δ=0.13 [s; 6H, ClSi(CH$_3$)$_2$], 0.61 (m; 2H, SiCH$_2$), 0.83, 1.18 [2s; 6H, gem-(CH$_3$)$_2$], 1.88 (s; 3H, CH$_3$—C≡C), 1.05–2.26 (m; 9H, CH, CH$_2$ pinane skeleton).

IR(KBr, cm$^{-1}$): 2188 (C≡C)

[α]$_D$= −3.49 (c=38.1 g/dl: toluene).

(3) Preparation of (+)-poly[1-(dimethyl(10-pinanyl)silyl)-1-propyne] [hereinafter referred to simply as (+)-poly(DPSP)]:

TaCl$_5$ (0.14 g, 38 mmol) was dissolved in toluene (6.0 ml) and thus solution A was obtained. Separately, (−)-(DPSP) (3.0 g; 12.8 mmol) was dissolved in toluene (4.5 ml) and thus solution B was obtained. To the solution A was added the solution B in nitrogen gas at 100° C. The mixture thus obtained was stirred for 27 hours and the reaction mixture was poured into methanol. The obtained polymer was dissolved in toluene and purified through reprecipitation from methanol.

$^1$H-NMR (CDCl$_3$): δ=0.21 [b; Si(CH$_3$)$_2$], 0.84, 1.17 [2b; gem-(CH$_3$)$_2$], 1.65 (b; CH$_3$—C≡C), 1.14–2.02 (b; CH, CH$_2$ pinane skeleton).

IR(KBr, cm$^{-1}$): 1566 (C=C)

[α]$_D$= +9.03 (c=0.94 g/dl: toluene).

The (+)-poly(DPSP) thus obtained was in the form of a white powder and had a weight-average molecular weight of $1.50 \times 10^5$.

Example 2

Production of (+)-poly(DPSP) membrane

The powder of (+)-poly(DPSP) (50 mg) obtained in Example 1 was dissolved in toluene (2.0 ml). The solution thus obtained was east on a polytetrafluoroethylene sheet stuck to a glass plate. After evaporating the toluene by allowing it to stand at room temperature for 24 hours, the membrane thus obtained was vacuum-dried at room temperature for 24 hours. After drying, the thickness of the membrane was 60 μm.

Example 3

(±)-Tryptophan (2.01 g, 9.84 mmol) was added to distilled water (400 ml). The obtained mixture was ultrasonicated while heated to about 40° C. and thus the (1) tryptophan was completely dissolved in distilled water (a 0.50 wt. % solution).

By using a glass permeation cell as shown in FIG. 1, an optical resolution experiment on (±)-tryptophan was carried out.

Namely, the (+)-poly(DPSP) membrane 1 obtained in Example 2 was put between packings and the glass cell was partitioned with this membrane into two parts, namely, the feed side 2 and the permeation side 3 which were filled respectively with the feed solution as prepared above and a pure solvent (water in this case), respectively. After the lapse of a given period of time, the liquid in the permeation side 3 was sampled. After sampling, the chamber of the permeation side 3 was immediately filled with the pure solvent. The solvent (water in this case) of the permeate was evaporated and the permeating solute was thus precipitated. Then the amount of the permeating solute was determined by weighing it. The optical purity of the permeating solute was determined by dissolving this solute in water and subjecting to HPLC provided with an optical resolution column (Chiralpak WH, mfd. by Daicel Chemical Industries, Ltd.).

The permeation constant P was calculated in accordance with the following formula:

$P = (Q \cdot L)/(A \cdot T \cdot \Delta C).$

P: permeation constant (m²/hr)
Q: weight of permeating solute (g)
L: membrane thickness (m)
A: permeation area (m²)
T: permeation time (hr)
ΔC: concentration gradient (g/m³).

As the result of the experiment, the permeation constant P was $0.12 \times 10^{-9}$ m²/hr and the optical purity was 80.7% ee.

Example 4

(±)-Tryptophan (0.158 g, 0.774 mmol) was dissolved in methanol (400 ml, 316 g). The mixture thus obtained was ultrasonicated while heated at about 40° C. to thereby completely dissolve the tryptophan (a 0.0500 wt. % solution). Subsequently, an optical resolution experiment was effected by repeating the procedure described in Example 3. As the result of the experiment, the permeation constant P was $5.16 \times 10^{-9}$ m²/hr and the optical purity was 96.2% ee.

Example 5

(±)-2-Butanol (12.4 g, 167 mmol) was added to distilled water (400 g) and the mixture thus obtained was stirred to thereby give a homogeneous solution (a 3.00 wt. % solution). Subsequently, an optical resolution experiment was effected by repeating the procedure described in Example 3. As the result of the experiment, the permeation constant P was $0.17 \times 10^{-9}$ m²/hr and the optical purity was 15.8% ee.

Example 6

(±)-Mandelic acid (4.04 g, 26.6 mmol) was dissolved in distilled water (400 g). The mixture thus obtained was ultrasonicated while heated at about 40° C. to thereby completely dissolve the mandelic acid (a 1.00 wt. % solution). Subsequently, an optical resolution experiment was effected by repeating the procedure described in Example 3. As the result of the experiment, the permeation constant P was $0.31 \times 10^{-9}$ m²/hr and the optical purity was 83.4% ee.

We claim:

1. An optically active acetylene polymer which is obtained by polymerizing an optically active form of 1-[dimethyl(10-pinanyl)silyl]-1-propyne, which is represented by the following formula (I) and has a weight-average molecular weight of from 10,000 to 1,000,000:

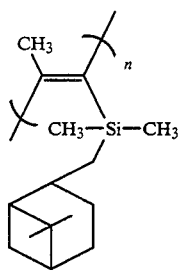

(I)

wherein n represents a number giving a weight-average molecular weight of from 10,000 to 1,000,000.

2. A membrane comprising as the main component an optically active acetylene polymer which is obtained by polymerizing an optically active form of 1-[dimethyl(10-pinanyl)silyl]-1-propyne, which is represented by the following formula (1) and has a weight-average molecular weight of from 10,000 to 1,000,000:

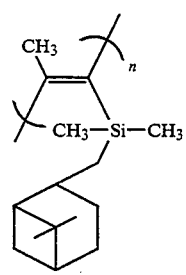

(I)

wherein n represents a number giving a weight-average molecular weight of from 10,000 to 1,000,000.

3. An optical resolution method which comprises optically resolving a mixture of optical isomers by using a membrane comprising as the main component an optically active acetylene polymer which is obtained by polymerizing an optically active form of 1-[dimethyl (10-pinanyl)silyl]-1-propyne, which is represented by the following formula (I) and has a weight-average molecular weight of from 10,000 to 1,000,000:

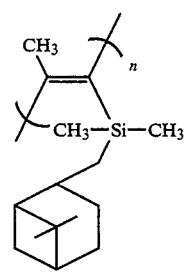

(I)

wherein n represents a number giving a weight-average molecular weight of from 10,000 to 1,000,000.

4. An optical resolution method as claimed in claim 3 wherein the solvent in which a mixture of optical isomers is to be dissolved is an aqueous solvent system.

5. An optical resolution method as claimed in claim 3 wherein the solvent in which a mixture of optical isomers is to be dissolved is a methanol solvent system.

* * * * *